United States Patent
Rivas Cardona et al.

(10) Patent No.: US 11,180,430 B2
(45) Date of Patent: Nov. 23, 2021

(54) OLEFIN OLIGOMERIZATION PROCESSES AND RELATED ZEOLITES AND STRUCTURE DIRECTING AGENTS

(71) Applicant: ExxonMobil Chemical Patents Inc., Baytown, TX (US)

(72) Inventors: Alejandra R. Rivas Cardona, Humble, TX (US); Allen W. Burton, Stewartsville, NJ (US); Sina Sartipi, Brussels (BE); Andrew D. Wiersum, Baton Rouge, LA (US); Lara A. Truter, Einhoven (NL); Marianne F. Smits, Mortsel (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/613,367

(22) PCT Filed: Apr. 30, 2018

(86) PCT No.: PCT/US2018/030079
§ 371 (c)(1),
(2) Date: Nov. 13, 2019

(87) PCT Pub. No.: WO2018/236471
PCT Pub. Date: Dec. 27, 2018

(65) Prior Publication Data
US 2020/0325084 A1    Oct. 15, 2020

Related U.S. Application Data

(60) Provisional application No. 62/524,096, filed on Jun. 23, 2017.

(51) Int. Cl.
*C07C 2/12* (2006.01)
*B01J 29/70* (2006.01)
(Continued)

(52) U.S. Cl.
CPC ............ *C07C 2/12* (2013.01); *B01J 29/7007* (2013.01); *B01J 35/1019* (2013.01);
(Continued)

(58) Field of Classification Search
CPC ....... C07C 2/12; C07C 11/02; C07C 2529/70; B01J 29/7007; B01J 35/1019;
(Continued)

(56) References Cited

U.S. PATENT DOCUMENTS

| | | | |
|---|---|---|---|
| 5,672,800 A | 9/1997 | Mathys et al. | |
| 6,143,942 A | 11/2000 | Verrelst et al. | |
| 6,699,811 B1 | 3/2004 | Mohr et al. | |

(Continued)

OTHER PUBLICATIONS

Higgins et al., "The Framework Topology of Zeolite Beta" Zeolites (1988), pp. 446-452, vol. 8.
(Continued)

*Primary Examiner* — Youngsul Jeong
*Assistant Examiner* — Jason Y Chong

(57) ABSTRACT

The disclosure relates to olefin oligomerization processes and related zeolites and structure directing agents. The olefin oligomerization processes can exhibit relatively high conversions. The zeolites can exhibit comparatively high stabilities. The zeolites can have relatively high ratios of external surface area to total surface area. An exemplary zeolite is a beta zeolite having a relatively high ratio of external surface area to total surface area. The disclosure also relates to structure directing agents, and methods of using the structure direction agents to prepare the zeolites.

24 Claims, 3 Drawing Sheets

(51) Int. Cl.
  B01J 35/10 (2006.01)
  C07D 401/06 (2006.01)
  C07C 11/02 (2006.01)
(52) U.S. Cl.
  CPC ........ B01J 35/1023 (2013.01); C07D 401/06 (2013.01); *C07C 11/02* (2013.01); *C07C 2529/70* (2013.01)
(58) Field of Classification Search
  CPC . B01J 35/1023; B01J 35/1061; C07D 401/06; C07D 211/06; C01B 39/48
  See application file for complete search history.

(56) References Cited

U.S. PATENT DOCUMENTS

| | | | |
|---|---|---|---|
| 6,884,914 B2 | 4/2005 | Mathys et al. | |
| 2011/0230690 A1* | 9/2011 | Tiita | C07C 2/12 585/255 |
| 2013/0324777 A1* | 12/2013 | Hanks | C10L 1/08 585/329 |

OTHER PUBLICATIONS

Lippens et al., "Studies on Pore Systems in Catalysts: V. the t Method" Journal of Catalysis (1965), pp. 319-323, vol. 4.
Newsam et al., "Structural Characterization of Zeolite Beta" Proc. R. Soc. Lond. A (1988), 420, pp. 375-405.
Blasco et al., "Unseeded Synthesis of Al-free Ti-beta Zeolite in Fluoride Medium: A Hydrophobic Selective Oxidation Catalyst" Chemical Communication (1996), pp. 2367-2368.
Martinez-Franco et al., "High-Silica Nanocrystalline Beta Zeolites: Efficient Synthesis and Catalytic Application" Chemical Science (2016) pp. 102-108, vol. 7.
Wulfers Matthew J. et al., "Assessment of mass transfer limitations in oligomerization of butene at high pressure on H-beta" Applied Catalysis A: General, Elsevier, Amsterdam, IL (Aug. 11, 2015), pp. 394-401, vol. 505.
A. Corma et al., "Alkylation of Benzene with Short-Chain Olefins over MCM-22 Zeolite: Catalytic Behaviour and Kinetic Mechanism", Journal of Catalysis., (May 1, 2000), pp. 163-173, vol. 192, No. 1.
Dong Ho Park et al., "Selective Isobutene Oligomerization by Mesoporous MSU-S BEA Catalysts" Journal of Physical Chemistry C (Mar. 11, 2011), pp. 5809-5816, vol. 115, No. 13.
Eva M. Gallego et al., "Simple organic structure directing agents for synthesizing nanocrystalline zeolites" Chemical Science, (Oct. 5, 2017), pp. 8138-8149, vol. 8, No. 12, UK.
M. Rocío Díaz-Rey et al., Efficient Oligomerization of Pentene into Liquid Fuels on Nanocrystalline Beta Zeolites, ACS Catalysis, 2017, pp. 6170-6178, vol. 7, No. 9 & Supporting information.

\* cited by examiner

OLEFIN OLIGOMERIZATION PROCESSES AND RELATED ZEOLITES AND STRUCTURE DIRECTING AGENTS

CROSS-REFERENCE TO RELATED APPLICATIONS

This application is a National Phase Application claiming priority to PCT Application Serial No. PCT/US2018/030079 filed Apr. 30, 2018, which claims priority to U.S. Provisional Application No. 62/524,096, filed Jun. 23, 2017, the disclosures of which are incorporated herein by reference.

FIELD OF THE INVENTION

The disclosure relates to olefin oligomerization processes, as well as related zeolites and structure directing agents.

BACKGROUND OF THE INVENTION

Zeolites are commonly used to catalyze olefin oligomerization. For example, zeolites are used to oligomerize propylene to hydrocarbons containing six or more carbon atoms. There remains a need, however, for improved zeolites and oligomerization processes that exhibit high catalyst stabilities and conversions.

References of interest may include: Mathys et al., U.S. Pat. No. 5,672,800; Verrelst et al., U.S. Pat. No. 6,143,942; Mathys et al., U.S. Pat. No. 6,884,914; Mohr et al., U.S. Pat. No. 6,699,811; Lippens et al., "Studies on Pore Systems in Catalysts: V. the t Method," *J. Catal.* 4, 319 (1965); Higgins et al., "The Framework Topology of Zeolite Beta," *Zeolites*, 8, 446-452 (1988); Newsam et al., "Structural Characterization of Zeolite Beta," *Proc. R. Soc. Lond. A*, 420, 375-405 (1988); Blasco et al., "Unseeded Synthesis of Al-free Ti-beta Zeolite in Fluoride Medium: A Hydrophobic Selective Oxidation Catalyst," *Chem. Commun.*, 2367-2368 (1996); and Martinez-Franco et al., "High-Silica Nanocrystalline Beta Zeolites: Efficient Synthesis and Catalytic Application," *Chem. Sci.*, 2016, 7, 102-108 (2016).

SUMMARY OF THE INVENTION

The disclosure provides olefin oligomerization processes that can exhibit high conversions. The disclosure also provides zeolites, including beta zeolites, which can be used in the oligomerization processes. The zeolites can have comparatively high stabilities. The zeolites can have relatively high ratios of external surface area to total surface area (ESA/TSA). The disclosure further provides structure directing agents and methods of using the structure directing agents to prepare such zeolites.

In an aspect, the disclosure provides a method of converting first olefin(s) to second olefin(s). The method includes contacting the first olefin(s) with a beta zeolite under oligomerization conditions to convert the first olefin(s) to the second olefin(s). The first olefin(s) has at most five carbon atoms, and the second olefin(s) has at least two more carbon atoms than the first olefin. The beta zeolite has a ratio of external surface area to total surface area of at least 0.4.

In another aspect, the disclosure provides a method of converting first olefin(s) to second olefin(s). The method includes contacting the first olefin(s) with a zeolite to convert the first olefin(s) to the second olefin(s). The first olefin(s) has at most five carbon atoms and the second olefin(s) has at least two more carbon atoms than the first olefin. The zeolite has a stability of at least 99.5% at a temperature of at least 180° C.

In a further aspect, the disclosure provides a method of converting first olefin(s) to second olefin(s). The method includes contacting the first olefin(s) with a zeolite to convert the first olefin(s) to the second olefin(s). The method is performed at a temperature of 150° C. The first olefin(s) has at most five carbon atoms and the second olefin(s) has at least two more carbon atoms than the first olefin(s). The zeolite has a stability of at least 92%.

In an aspect, the disclosure provides a method of converting first olefin(s) to second olefin(s). The method includes contacting the first olefin(s) with a zeolite to convert the first olefin to the second olefin(s) at a conversion of 85%. The first olefin(s) has at most five carbon atoms and the second olefin(s) has at least two more carbon atoms than the first olefin(s).

In another aspect, the disclosure provides a method of converting first olefin(s) to second olefin(s). The method includes contacting the first olefin(s) with a zeolite to convert the first olefin(s) to the second olefin(s). The first olefin(s) has at most five carbon atoms. The second olefin(s) has at least two more carbon atoms than the first olefin(s). The zeolite is a first beta zeolite having a ratio of external surface area to total surface area that is at least 0.6. The first beta zeolite has a stability that is greater than a stability of a second beta zeolite having a ratio of external surface area to total surface area that is less than 0.6. For example, the first beta zeolite can have a stability that is at least 5% greater than a stability of the second beta zeolite.

In a further aspect, the disclosure provides a beta zeolite having ESA/TSA ratio of at least 0.6, such as at least 0.65 (e.g., or at least 0.7).

In an additional aspect, the disclosure provides a compound having the structure:

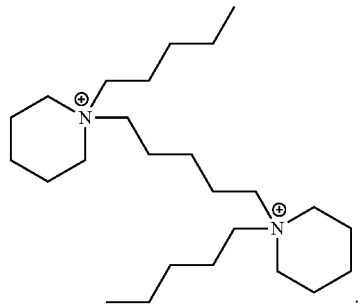 [SMILES: CCCCC[N+]1(CCCCC[N+]2(CCCCC)CCCCC2)CCCCC1]

In an aspect, the disclosure provides a method that includes using a compound to make a zeolite, the compound having the structure:

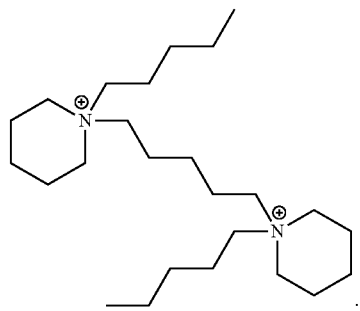 [SMILES: CCCCC[N+]1(CCCCC[N+]2(CCCCC)CCCCC2)CCCCC1]

DETAILED DESCRIPTION OF PREFERRED EMBODIMENTS

Definitions

Figure 1:
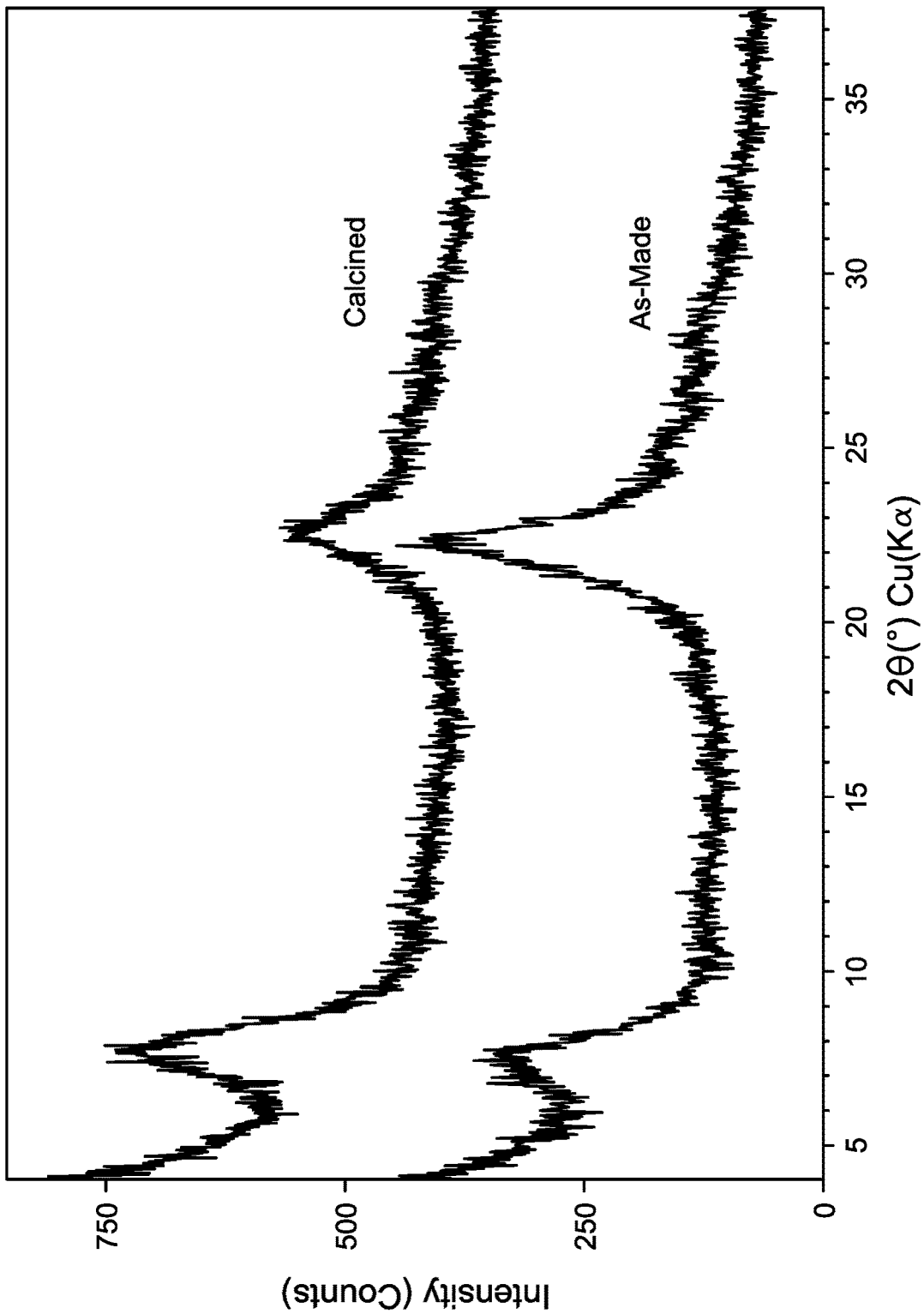
FIG. 1 shows X-ray powder diffraction patterns of an as-made and calcined zeolite.

As used herein, "conversion" refers to a single-pass conversion defined as:

1−(y/x), wherein

"x" is the concentration in weight percent of first olefin(s) fed to a reaction zone based on the total amount of hydrocarbons provided to the reaction zone; and "y" is the concentration in weight percent of the first olefin(s) recovered from the reaction zone based on the total amount of hydrocarbons recovered from the reaction zone.

As used herein, conversion is given as a percentage. For example, in the case of propylene oligomerization, a conversion of at least 25% means that at least 25% of propylene provided to a reaction zone was converted, in a single pass within the reaction zone, to a hydrocarbon other than propylene. For example, in the case of oligomerization of a mixture of propylene, butylene, and pentene, a conversion of at least 25% means that at least 25% of the total amount of the propylene, butylene, and pentene provided to a reaction zone was converted, in a single pass within the reaction zone, to hydrocarbon(s) other than propylene, butylene, and pentene.

As used herein, the term "selectivity" means the weight of hydrocarbon product that has a certain number of carbon atoms divided by the total weight of hydrocarbon product. For example, a selectivity of 27 weight percent for hydrocarbons having from five carbon atoms to seven carbon atoms means that 27 weight percent of the total hydrocarbon product has from five carbon atoms to seven carbon atoms.

As used herein, "stability" means the ability of the catalyst at a given process temperature to maintain its initial olefin conversion after being exposed to 6 grams per hour of feed for 48 hours. For example, a zeolite with a stability of 99.9% at a given process temperature is a zeolite that is able to maintain 99.9% of its initial conversion after being exposed to six grams per hour of feed for 48 hours at the given temperature.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. The term "$C_n$" means hydrocarbon(s) having n carbon atom(s) per molecule, wherein n is a positive integer.

The term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane, and octane. "Alkane" is intended to embrace all structural isomeric forms of an alkane. For example, butane encompasses n-butane and isobutane; pentane encompasses n-pentane, isopentane, and neopentane.

As used herein, the term "olefin" refers to a branched or unbranched unsaturated hydrocarbon having one or more carbon-carbon double bonds. A simple olefin comprises the general formula $C_nH_{2n}$, where n is 2 or greater. Examples of olefins include, but are not limited to ethylene, propylene, butylene, pentene, hexene, and heptene. "Olefin" is intended to embrace all structural isomeric forms of an olefin. For example, butylene encompasses but-1-ene, (Z)-but-2-ene, etc.

The term "aromatic" means a planar cyclic hydrocarbyl with conjugated double bonds, such as, for example, benzene. As used herein, the term aromatic encompasses compounds containing one or more aromatic rings, including, but not limited to, benzene, toluene, and xylene, and polynuclear aromatics (PNAs), which include, but are not limited to, naphthalene, anthracene, chrysene, and their alkylated versions.

As referred to herein, the total surface area ($S_{BET}$) of a zeolite is measured by the Brunauer-Emmett-Teller (BET) method using adsorption-desorption of nitrogen (temperature of liquid nitrogen, 77 K) method as discussed in Lippens and de Boer, "Studies on Pore Systems in Catalysts: V. the t Method" J. Catal, 1965, 4, 319.

As referred to herein, the external surface area of a zeolite is determined by subtracting the internal surface area of the zeolite (determined using the t-plot method as discussed in Lippens and de Boer, "Studies on Pore Systems in Catalysts: V. the t Method" J. Catal, 1965, 4, 319) from the total surface area of the zeolite.

Oligomerization Process

In general, the olefin oligomerization processes disclosed herein involve oligomerizing first olefin(s) having at most five carbon atoms to second olefin(s) having at least two more carbon atoms than the first olefin(s). For example, if the first olefin is propylene, then the second olefin has at least five carbon atoms.

An olefin having at most five carbon atoms can have two carbon atoms, three carbon atoms, four carbon atoms, or five carbon atoms. Examples of such olefins include ethylene, propylene, butylene, and pentylene. Suitable olefins having at most five carbon atoms may be linear or branched. Preferably, suitable olefins having at most five carbon atoms are non-aromatic.

An olefin having at least six carbon atoms can have, for example, six carbon atoms, seven carbon atoms, eight carbon atoms, nine carbon atoms, 10 carbon atoms, 11 carbon atoms, 12 carbon atoms, 13 carbon atoms, 14 carbon atoms, 15 carbon atoms, or more carbon atoms. Suitable olefins having at least six carbon atoms may be linear or branched. Preferably, suitable olefins having at least six carbon atoms are non-aromatic.

Oligomerization processes disclosed herein can involve conversion by side reactions such as cracking and/or re-oligomerization to third olefin(s) having at least five carbon atoms. In some embodiments, an oligomerization process can result in the formation of a product that includes a mixture of olefins having different numbers of carbon atoms. As an example, when oligomerizing propylene, the product may contain a mixture of olefins, including olefins with six carbon atoms, olefins with nine carbon atoms, olefins with 12 carbon atoms, and olefins with 15 carbon atoms. In certain embodiments, a propylene oligomerization process with a zeolite (e.g., beta zeolite) disclosed herein can exhibit selectivity for certain mixtures of olefins having at least five carbon atoms. In some embodiments, the products of propylene oligomerization include from five weight percent to 30 weight percent (e.g., from 10 weight percent to 30 weight percent) olefins having from five carbon atoms to seven carbon atoms, from 50 weight percent to 80 weight percent (e.g., from 60 weight percent to 80 weight percent) olefins having from eight carbon atoms to 10 carbon atoms, and from three weight percent to 35 weight percent (e.g., from three weight percent to 20 weight percent) olefins having at least 11 carbon atoms. For example, the products of propylene oligomerization can include from 11 weight percent to 27 weight percent olefins having from five carbon atoms to seven carbon atoms, from 61 weight percent to 78 weight percent olefins having from eight carbon atoms to 10 carbon atoms, and from three weight percent to 18 weight percent olefins having at least 11 carbon atoms.

In any embodiment, olefins produced by the oligomerization processes described herein may be subsequently subjected to hydroformylation for the production of aldehydes and alcohols, which are themselves useful in the production of plasticizers, mercaptans, adhesives, and surfactants.

Typically, an oligomerization process involves using a zeolite, such as a beta zeolite, as a catalyst. Discussion of the framework of beta zeolite may be found in the following references: Higgins et al., "The framework topology of zeolite beta," Zeolites, 8, 446-452 (1988); Newsam et al., "Structural characterization of zeolite beta," Proc. R. Soc. Lond. A, 420, 375-405 (1988); and Blasco et al., "Unseeded synthesis of Al-free Ti-beta zeolite in fluoride medium: A hydrophobic selective oxidation catalyst" Chem. Commun., 2367-2368 (1996).

In certain embodiments, the zeolite (e.g., beta zeolite) has a relatively high ratio of its external surface area to total surface area. For example, the ratio of external surface area to total surface area can be at least 0.4 (e.g., at least 0.45, at least 0.5, at least 0.55, at least 0.6, at least 0.65, at least 0.7).

In some embodiments, the zeolite (e.g., beta zeolite) has a total surface area of at least 600 m$^2$/gram (e.g., at least 650 m$^2$/gram, at least 700 m$^2$/gram, at least 725 m$^2$/gram), and/or a total surface area of at most 900 m$^2$/gram (e.g., at most 850 m$^2$/gram, at most 800 m$^2$/gram, at most 775 m$^2$/gram). For example, the zeolite (e.g., beta zeolite) can have a total surface area of from 600 m$^2$/gram to 900 m$^2$/gram (e.g., from 700 m$^2$/gram to 800 m$^2$/gram, from 725 m$^2$/gram to 775 m$^2$/gram).

In certain embodiments, the zeolite (e.g., beta zeolite) has an external surface area of at least 450 m$^2$/gram (e.g., at least 500 m$^2$/gram, at least 525 m$^2$/gram), and/or an external surface area of at most 650 m$^2$/gram (e.g., at most 600 m$^2$/gram, at most 575 m$^2$/gram). For example, the zeolite (e.g., beta zeolite) can have an external surface area of from 450 m$^2$/gram to 650 m$^2$/gram (e.g., from 500 m$^2$/gram to 600 m$^2$/gram, from 525 m$^2$/gram to 575 m$^2$/gram).

In general, the Si/Al$_2$ ratio of the zeolite (e.g., beta zeolite) is at most 120 (e.g., at most 110, at most 100, at most 90, at most 80, at most 70, at most 60, at most 50), and/or at least 15 (e.g., at least 20, at least 25). As an example, the Si/Al$_2$ ratio of the zeolite (e.g., beta zeolite) can be from 15 to 120 (e.g., from 20 to 70, from 25 to 50).

Typically, a crystal of the zeolite (e.g., beta zeolite) has a length that is from 50 nanometers to 150 nanometers, a width that is from six nanometers to 15 nanometers, and a thickness that is less than 10 nanometers (e.g., from four nanometers to six nanometers).

In general, the olefin oligomerization processes disclosed herein are conducted under oligomerization conditions. Typically, the oligomerization conditions comprise a temperature of at least 130° C. (e.g., at least 140° C., at least 150° C.) and/or at most 300° C. (e.g., at most 230° C., at most 200° C., at most 180° C.). For example, an oligomerization process can be conducted at a temperature of from 130° C. to 300° C. (e.g., from 150° C. to 300° C., from 150° C. to 250° C., from 150° C. to 230° C.). Typically, the oligomerization conditions further comprise a pressure of at least 50 bar (e.g., at least 60 bar) and/or at most 100 bar (e.g., at most 80 bar). For example, an oligomerization process can be conducted at a pressure of from 50 bar to 100 bar (e.g., from 60 bar to 100 bar, from 60 bar to 80 bar).

Typically, the olefin oligomerization processes disclosed herein are conducted by providing a feed that contains the olefin(s) having at most five hydrocarbons. The feed is contacted with the zeolite (e.g., beta zeolite) in an appropriate vessel (e.g., a stainless steel vessel) to yield the oligomerization reaction product(s).

The olefin oligomerization processes disclosed herein may be batch, semi-batch, continuous, or semi-continuous processes, preferably continuous processes. Generally, in continuous processes the feed is provided to the vessel over time at an appropriate weight hourly space velocity. In some embodiments, the weight hourly space velocity is from 0.1 hour$^{-1}$ to 20 hours$^{-1}$.

In general, the feed contains additional hydrocarbons beyond just the olefin(s) having at most five hydrocarbons. The additional hydrocarbons can include one or more saturated hydrocarbons (e.g., one or more alkanes) and/or unsaturated hydrocarbons (e.g., one or more olefinic hydrocarbons). Examples of saturated hydrocarbons include alkanes having from two carbon atoms to five carbon atoms, such as, for example, ethane, propane, butane, pentane, and isobutane. Examples of unsaturated hydrocarbons include olefinic hydrocarbons having from two carbon atoms to five carbon atoms, such as, for example, ethylene, butylene, propylene, and pentylene. In some embodiments, the feed contains from 35 weight percent to 65 weight percent (e.g., from 40 weight percent to 60 weight percent, from 45 weight percent to 55 weight percent) olefinic hydrocarbon(s).

Optionally, the feed may also include up to 60 weight percent aromatics, such as, for example, up to 40 weight percent aromatics, and/or include at least 1 weight percent aromatics, such as at least 10 weight percent aromatics. Alternatively, the feed may be free of aromatics, i.e., the feed may include 0 weight percent aromatics.

The olefin oligomerization processes disclosed herein can have a conversion of at least 25% (e.g., at least 50%, at least 75%, at least 85%, at least 90%, at least 95%, at least 98%) under temperature and pressure conditions noted above.

In some embodiments, for the same olefin oligomerization process run under the same conditions, using a given zeolite results in a conversion that is greater than that achieved when using a zeolite having the same framework structure but a lower ratio of external surface area to total surface area. As an example, for the same olefin oligomerization process run under the same conditions, using a beta zeolite having a ratio of external surface area to total surface area that is greater than 0.4 can result in a conversion that is greater (e.g., at least 5% greater, at least 10% greater, at least 15% greater, at least 20% greater, at least 25% greater) than when using a beta zeolite having the same framework structure but a ratio of external surface area to total surface area that is less than 0.4. As another example, for the same olefin oligomerization process run under the same conditions, using a beta zeolite having a ratio of external surface area to total surface area that is greater than 0.45 can result in a conversion that is greater (e.g., at least 5% greater, at least 10% greater, at least 15% greater, at least 20% greater, at least 25%) than when using a beta zeolite having the same framework structure but a ratio of external surface area to total surface area that is less than 0.45. As yet another example, for the same olefin oligomerization process run under the same conditions, using a beta zeolite having a ratio of external surface area to total surface area that is greater than 0.5 can result in a conversion that is greater (e.g., at least 5% greater, at least 10% greater, at least 15% greater, at least 20% greater, at least 25%) than when using a beta zeolite having the same framework structure but a ratio of external surface area to total surface area that is less than 0.5. As a further example, for the same olefin oligomerization process run under the same conditions, using a beta zeolite having a ratio of external surface area to total surface area that is greater than 0.55 can result in a conversion that is greater (e.g., at least 5% greater, at least 10% greater, at least 15% greater, at least 20% greater, at least 25%) than when using a beta zeolite having the same framework structure but a ratio of external surface area to total surface area that is less than 0.55. As still a further example, for the same olefin oligomerization process run under the same conditions, using a beta zeolite having a ratio of external surface area to total surface area that is greater than 0.6 can result in a conversion that is greater (e.g., at least 5% greater, at least 10% greater, at least 15% greater, at least 20% greater, at least bout 25%) than when using a beta zeolite having the same framework structure but a ratio of external surface area to total surface area that is less than 0.6. As another, for the same olefin oligomerization process run under the same conditions, using a beta zeolite having a ratio of external surface area to total surface area that is greater than 0.65 can result in a conversion that is greater (e.g., at least 5% greater, at least 10% greater, at least 15% greater, at least 20% greater, at least 25%) than when using a beta zeolite having the same framework structure but a ratio of external surface area to total surface area that is less than 0.65. As a further example, for the same olefin oligomerization process run under the same conditions, using a beta zeolite having a ratio of external surface area to total surface area that is greater than 0.7 can result in a conversion that is greater (e.g., at least 5% greater, at least 10% greater, at least 15% greater, at least 20% greater, at least bout 25%) than when using a beta zeolite having the same framework structure but a ratio of external surface area to total surface area that is less than 0.7.

The zeolite (e.g., beta zeolite) can have a stability of at least 90% (e.g., at least 92%, at least 95%, at least 98%, at least 99%, at least 99.5%) under temperature and pressure conditions noted above.

In some embodiments, for the same olefin oligomerization process run under the same conditions, a zeolite can have a stability that is greater than the stability of a zeolite having the same framework structure but a lower ratio of external surface area to total surface area. As an example, for the same olefin oligomerization process run under the same conditions, a beta zeolite having a ratio of external surface area to total surface area that is greater than 0.4 can have a stability that is greater (e.g., at least 0.5% greater, at least 1% greater, at least 2% greater, at least 5% greater) than the stability of a beta zeolite having the same framework structure but a ratio of external surface area to total surface area that is less than 0.4. As another example, for the same olefin oligomerization process run under the same conditions, a beta zeolite having a ratio of external surface area to total surface area that is greater than 0.45 can have a stability that is greater (e.g., at least 0.5% greater, at least 1% greater, at least 2% greater, at least 5% greater) than the stability of a beta zeolite having the same framework structure but a ratio of external surface area to total surface area that is less than 0.45. As yet another example, for the same olefin oligomerization process run under the same conditions, a beta zeolite having a ratio of external surface area to total surface area that is greater than 0.5 can have a stability that is greater (e.g., at least 0.5% greater, at least 1% greater, at least 2% greater, at least 5% greater) than the stability of a beta zeolite having the same framework structure but a ratio of external surface area to total surface area that is less than 0.5. As a further example, for the same olefin oligomerization process run under the same conditions, a beta zeolite having a ratio of external surface area to total surface area that is greater than 0.55 can have a stability that is greater (e.g., at least 0.5% greater, at least 1% greater, at least 2% greater, at least 5% greater) than the stability of a beta zeolite having the same framework structure but a ratio of external surface area to total surface area that is less than 0.55. As still a further example, for the same olefin oligomerization process run under the same conditions, a beta zeolite having a ratio of external surface area to total surface area that is greater than 0.6 can have a stability that is greater (e.g., at least 0.5% greater, at least 1% greater, at least 2% greater, at least 5% greater) than the stability of a beta zeolite having the same framework structure but a ratio of external surface area to total surface area that is less than 0.6. As another, for the same olefin oligomerization process run under the same conditions, a beta zeolite having a ratio of external surface area to total surface area that is greater than 0.65 can have a stability that is greater (e.g., at least 0.5% greater, at least 1% greater, at least 2% greater, at least 5% greater) than the stability of a beta zeolite having the same framework structure but a ratio of external surface area to total surface area that is less than 0.65. As a further example, for the same olefin oligomerization process run under the same conditions, a beta zeolite having a ratio of external surface area to total surface area that is greater than 0.7 can have a stability that is greater (e.g., at least 0.5% greater, at least 1% greater, at least 2% greater, at least 5% greater) than the stability of a beta zeolite having the same framework structure but a ratio of external surface area to total surface area that is less than 0.7.

Typically, the zeolite (e.g., beta zeolite) is made using an organic structure directing agent (SDA). An example of such an SDA is 1,1'-(pentane-1,5-diyl)bis(1-pentylpiperidinium), which has the following molecular structure.

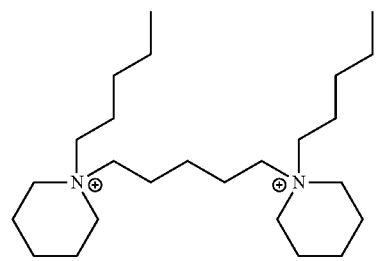 [SMILES: CCCCC[N+]1(CCCCC[N+]2(CCCCC)CCCCC2)CCCCC1]

In certain embodiments, the process of making 1,1'-(pentane-1,5-diyl)bis(1-pentylpiperidinium) involves first making N-pentylpiperidine (see discussion below).

Generally, a zeolite (e.g., beta zeolite) can be prepared as follows. A source of aluminum (e.g., aluminum isopropoxide) is dissolved in a solution that contains the SDA in its hydroxide form. A source of silicon (e.g., tetramethylorthosilicate) is added to the mixture, typically with stirring. A period of time is allowed to pass to allow appropriate for hydrolysis to occur. After that, water is added to bring the $H_2O/SiO_2$ ratio to an appropriate level. The mixture is then put in an appropriate vessel (e.g., capped Teflon liner) and put into an autoclave at an appropriate temperature (e.g., from 130° C. to 180° C.) for an appropriate period of time (e.g., from 10 days to 30 days), typically under tumbling conditions. The solid product is recovered (e.g., by filtration) and washed (e.g., with deionized water). The washed product is then dried (e.g., in an oven at from 50° C. to 100° C.). Organic material (e.g., remaining SDA) is removed from the zeolite by heating (e.g., at a temperature of 500° C. to 800° C.).

The following examples illustrate the present invention. Numerous modifications and variations are possible and it is to be understood that within the scope of the appended claims, the invention may be practiced otherwise than as specifically described herein.

EXAMPLES

Example 1: SDA Synthesis

N-pentylpiperidine was synthesized as follows.

To 500 milliliters of tetrahydrofuran (THF) in a 2000 milliliter Erlenmeyer flask was added 31.87 grams of valeraldehyde (0.37 mol). To this solution was then added 29.80 grams of piperdine (0.35 mol). Next 100 grams of sodium triacetoxyborohydride (0.47 mol) powder was added in 5-10 g increments. During the addition vigorous stirring was used to ensure that the powder did not clump at the bottom of the flask and for efficient mixing of the suspension. After each addition of the sodium triacetoxyborohydride powder, adequate time was provided to form a uniform slurry before the next addition of the powder. After one day, the product was worked up by quenching the suspension with the dropwise addition of 291 grams of a 27% KOH solution. The product was then extracted from the resultant solution with 500 milliliters of pentane. The organic fraction was then collected with a separatory funnel and dried with anhydrous magnesium sulfate. The N-pentylpyrrolidine product was then isolated by rotary evaporation of the THF and pentane solvents under reduced pressure. The yield was 55.5 g (92%).

The SDA was formed from the reaction between of N-pentylpiperdine and 1,5-dibromopentane.

55.5 grams of N-pentylpiperidine (0.35 mol) was added to 100 milliliters of acetonitrile inside a 500 milliliter round-bottom flask. 35.56 grams of 1,5-dibromopentane (0.155 mol) was dissolved in 60 milliliters of acetonitrile and then added dropwise to the amine solution. The resulting solution was refluxed for three days. The solid product was then collected by filtration and washed with acetone and then with ethyl ether. $^1$H and $^{13}$C NMR of the product showed the product to be pure.

The dibromide salt was then ion-exchanged into the hydroxide form by dissolving it in water and adding it to a two-fold excess of Dowex LC NG hydroxide exchange resin. The resin was then removed by filtration and washed with deionized water to remove the product from the resin. The aqueous fractions were then combined and concentrated under reduced pressure at 60° C. The hydroxide concentration of this aqueous solution ($[OH^-]$=1.08 millimoles/gram) was determined by titration with a standard solution of 0.1 N hydrochloric acid.

The product, 1,1'-(pentane-1,5-diyl)bis(1-pentylpiperidinium), has the following molecular structure.

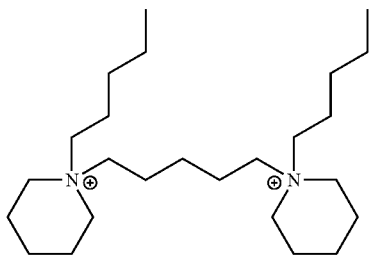 [SMILES: CCCCC[N+]1(CCCCC[N+]2(CCCCC)CCCCC2)CCCCC1]

Example 2: Zeolite Synthesis

A beta zeolite was prepared as follows.

Within a tared vessel, 1.35 grams aluminum isopropoxide was dissolved in 73.7 grams of a solution of the SDA (N-pentylpiperidine) in its hydroxide form ($[OH^-]$=0.68 millimole/gram). 15.23 grams of tetramethylorthosilicate was then added to the mixture and the resulting mixture was stirred thoroughly. At this point, the suspension was placed within a vented fume hood over the course of three days to allow the complete hydrolysis of the silica and alumina sources and to allow evaporation of water and the resultant methanol from the hydrolysis. At this point, deionized water was added to the suspension to bring the molar $H_2O/SiO_2$ ratio to 20. The mixture was then placed within a 125 milliliter Teflon liner, which was capped and then placed inside a sealed steel Parr autoclave. The autoclave was placed within a convection oven at 150° C. under tumbling conditions. After 21 days, the reactor was removed from the oven and quenched to room temperature. The solid product was recovered by filtration and washed with 1000 milliliters of deionized water. The product was then dried in an oven at 80° C. Powder XRD showed the material to be a beta product with very broad peaks in the pattern. The organic was removed from the zeolite by calcination to 600° C.

FIG. 1 shows X-ray powder diffraction patterns for the as-made and calcined zeolite. From FIG. 1, it was determined that the zeolite is a beta zeolite. The $Si/Al_2$ ratio of the beta zeolite was determined to 30. The product had a total surface area of 757 m$^2$/gram and an external surface area of 556 m$^2$/gram. The ratio of external surface area to total surface area was 0.734.

Example 3: Propylene Oligomerization

Figure 2:
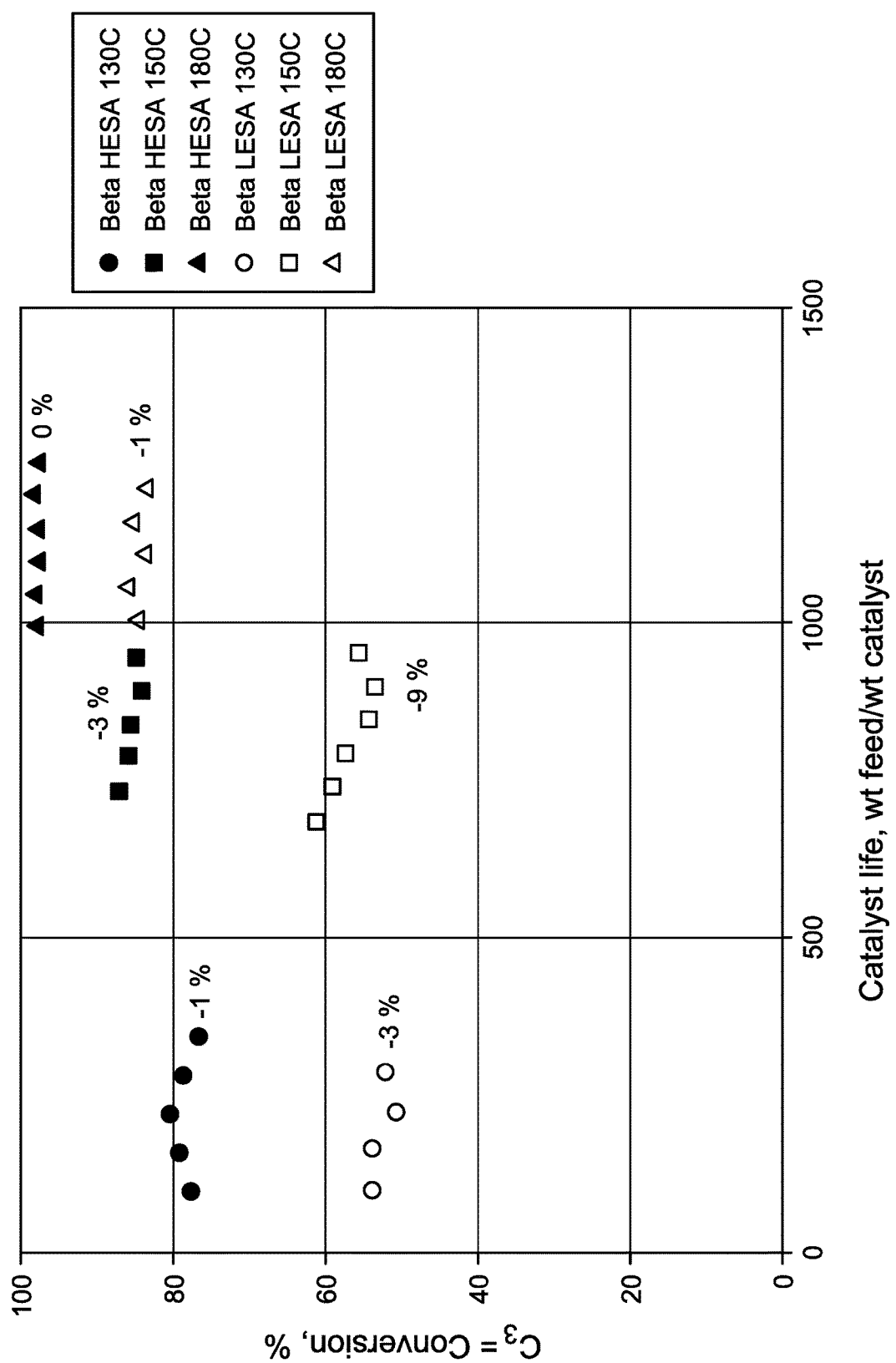
FIG. 2 is a graph that shows conversion for a propylene oligomerization process, as a function of catalyst life, under different process conditions.
Figure 3:
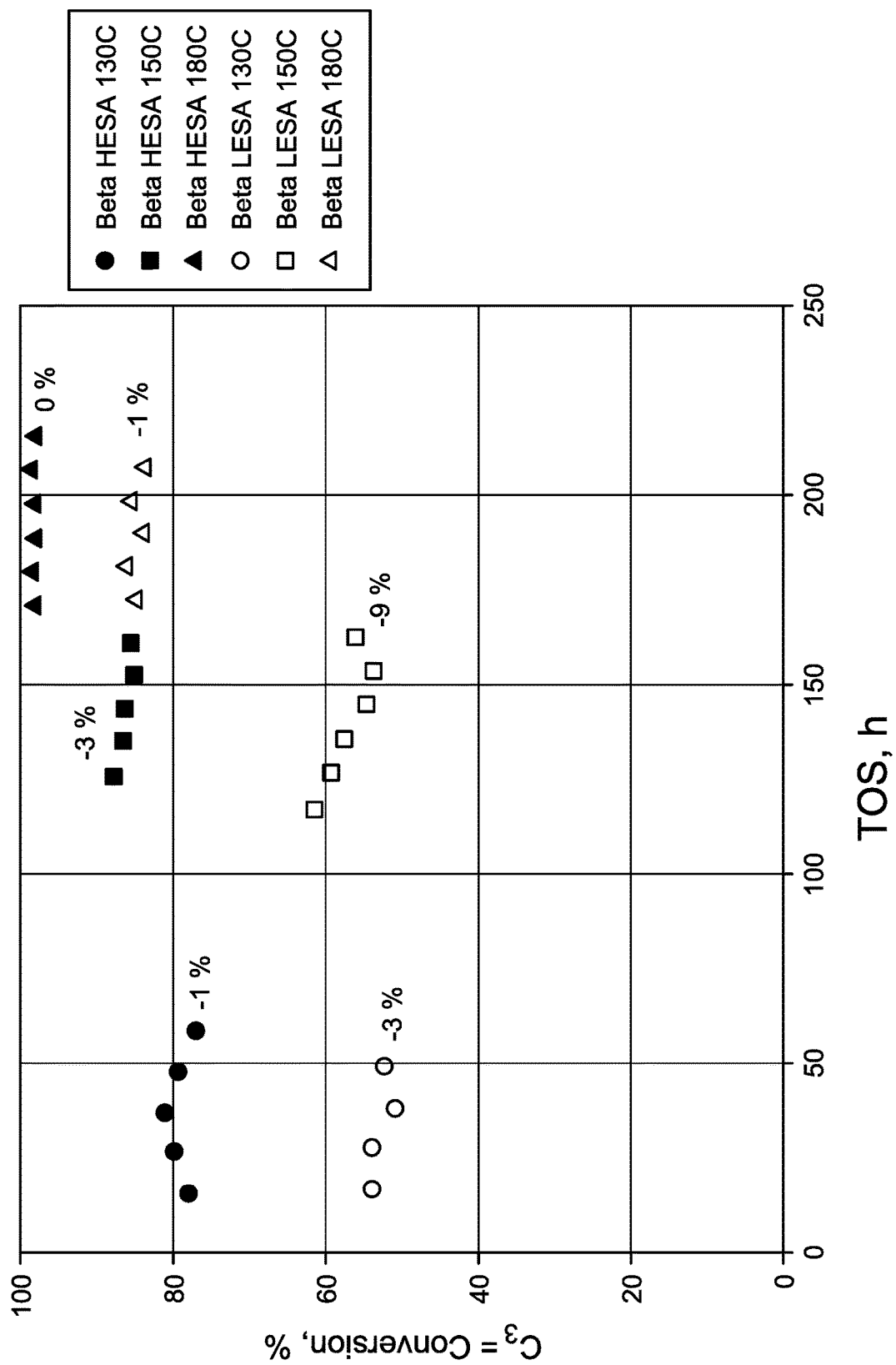
FIG. 3 is a graph that shows conversion for the same propylene oligomerization process but as a function of time on stream.

The calcined beta zeolite was pressed, crushed, and sieved to a particle size of 03-0.6 millimeter. One gram of the sized material was combined with inert and packed in a fix bed stainless steel reactor for oligomerization reaction testing. A mixture consisting of 50% propylene, 40% propane, and 10% isobutane (added as standard) was passed over the catalyst at a weight hourly space velocity of 6 hours$^{-1}$. The reactor was kept at a pressure of 70 bar and the temperature was varied between 80° C. and 200° C. Table 1 and FIG. 2 show the conversion as a function of catalyst life at 130° C., 150° C., and 180° C. Table 2 and FIG. 3 shows the conversion as a function of time on stream at 130° C., 150° C., and 180° C. In FIG. 2 and FIG. 3, the percentages represent the loss of propylene conversion from the start to the end of the run at a given temperature.

For the purpose of comparison, the same propylene oligomerization process was conducted using a comparative beta zeolite. The comparative beta zeolite had the same framework structure as the synthesized beta zeolite discussed in the preceding paragraph. However, the comparative beta zeolite had a Si/$Al_2$ ratio of 20, a total surface area of 725 $m^2$/gram, an external surface area of 297 $m^2$/gram, and a ratio of external surface area to total surface area was 0.410. Table 1 and FIG. 2 show the conversion as a function of catalyst life at 130° C., 150° C., and 180° C. Table 2 and FIG. 3 shows the conversion as a function of time on stream at 130° C., 150° C., and 180° C.

Table 3 provides stability values for the two zeolites as a function of temperature.

TABLE 1

| Material | Temperature, C. | Catalyst life, wt feed/wt catalyst | Conversion, % |
|---|---|---|---|
| Beta HESA (high external surface area) | 130 | 94.8 | 77.71 |
| | | 156.7 | 79.6 |
| | | 218.6 | 80.6 |
| | | 280.4 | 78.95 |
| | | 342.2 | 76.8 |
| | 150 | 731.7 | 87.47 |
| | | 783.7 | 86.1 |
| | | 835.7 | 85.8 |
| | | 887.9 | 84.61 |
| | | 939.9 | 85.11 |
| | 180 | 992.0 | 98.3 |
| | | 1044.1 | 98.57 |
| | | 1096.1 | 98.14 |
| | | 1148.2 | 98.16 |
| | | 1200.3 | 98.77 |
| | | 1252.3 | 98.06 |
| Beta LESA (low external surface area) | 130 | 100.4 | 53.78 |
| | | 162.5 | 53.78 |
| | | 224.7 | 50.92 |
| | | 287.0 | 52.13 |
| | 150 | 683.6 | 61.33 |
| | | 740.8 | 59.06 |
| | | 793.2 | 57.23 |
| | | 845.6 | 54.27 |
| | | 897.9 | 53.57 |
| | | 950.3 | 55.8 |
| | 180 | 1002.7 | 85.1 |
| | | 1055.1 | 86.4 |
| | | 1107.4 | 84.39 |
| | | 1159.9 | 85.66 |
| | | 1212.2 | 83.97 |

TABLE 2

| Material | Temperature, C. | TOS, h | Conversion, % |
|---|---|---|---|
| Beta HESA (high external surface area) | 130 | 16.28 | 77.71 |
| | | 26.9 | 79.6 |
| | | 37.52 | 80.6 |
| | | 48.13 | 78.95 |
| | | 58.75 | 76.8 |
| | 150 | 125.6 | 87.47 |
| | | 134.53 | 86.1 |
| | | 143.47 | 85.8 |
| | | 152.42 | 84.61 |
| | | 161.35 | 85.11 |
| | 180 | 170.3 | 98.3 |
| | | 179.23 | 98.57 |
| | | 188.17 | 98.14 |
| | | 197.1 | 98.16 |
| | | 206.05 | 98.77 |
| | | 214.98 | 98.06 |

TABLE 2-continued

| Material | Temperature, C. | TOS, h | Conversion, % |
|---|---|---|---|
| Beta LESA (low external surface area) | 130 | 17.13 | 53.78 |
| | | 27.73 | 53.78 |
| | | 38.35 | 50.92 |
| | | 48.98 | 52.13 |
| | 150 | 116.67 | 61.33 |
| | | 126.43 | 59.06 |
| | | 135.37 | 57.23 |
| | | 144.32 | 54.27 |
| | | 153.25 | 53.57 |
| | | 162.18 | 55.8 |
| | 180 | 171.13 | 85.1 |
| | | 180.07 | 86.4 |
| | | 189 | 84.39 |
| | | 197.95 | 85.66 |
| | | 206.88 | 83.97 |

TABLE 3

| | Stability | | |
|---|---|---|---|
| Temperature | 130° C. | 150° C. | 180° C. |
| Beta HESA | 98.6% | 96.5% | 99.9% |
| Beta LESA | 93.6% | 90.8% | 98.2% |

From Table 1, Table 2, Table 3, and FIG. 2 and FIG. 3, it is apparent that the conversion and stability achieved for the beta zeolite having the higher ratio of external surface area to total surface area were superior to that achieved for the beta zeolite having the lower ratio of external surface area to total surface area. The superior results were achieved even though the beta zeolite with the higher ratio of external surface area to total surface area had a lower Si/$Al_2$ ratio than the beta zeolite with the lower ratio of external surface area to total surface area.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. For example, the compositions described herein may be free of any component, or composition not expressly recited or disclosed herein. Any method may lack any step not recited or disclosed herein. Likewise, the term "comprising" is considered synonymous with the term "including." And whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A method of converting first olefin(s) to second olefin(s), the method comprising:
   contacting the first olefin(s) with a beta zeolite under oligomerization conditions to convert the first olefin(s) to the second olefin(s),
   wherein the first olefin(s) comprises at least one member selected from the group consisting of propylene, butylene, pentene, and mixtures thereof, the second olefin(s) comprises at least two more carbon atoms than the first olefin(s), and the beta zeolite has a ratio of external surface area to total surface area of at least 0.65.

2. The method of claim 1, wherein the conversion is at least 85%.

3. The method of claim 1, wherein the method produces a product comprising from 5 weight percent to 30 weight percent olefins having from five carbon atoms to seven carbon atoms, from 50 weight percent to 80 weight percent olefins having from eight carbon atoms to 10 carbon atoms, and from 3 weight percent to 35 weight percent olefins having at least 11 carbon atoms.

4. The method of claim 1, wherein a product of the method comprises a mixture of olefins comprising from five carbon atoms to 15 carbon atoms.

5. The method of claim 1, wherein the ratio of external surface area to total surface area is at least 0.7.

6. The method of claim 1, wherein the beta zeolite has an external surface area of at least 450 m$^2$/gram.

7. The method of claim 1, wherein the beta zeolite has a total surface area of at least 600 m$^2$/gram.

8. The method of claim 1, wherein a feed comprises the first olefin(s) and the method comprises contacting the beta zeolite with the feed to convert the first olefin(s) to the second olefin(s).

9. The method of claim 8, wherein the feed further comprises at least one alkane.

10. The method of claim 8, wherein the feed comprises from 35 weight percent to 65 weight percent olefinic hydrocarbons.

11. The method of claim 1, wherein the method is performed at a temperature of at least 130° C. and/or a temperature of at most 300° C.

12. The method of claim 11, wherein the method is performed at a temperature of at least 150° C.

13. The method of claim 1, wherein the method is performed at a pressure of at least 50 bar.

14. The method of claim 13, wherein the method is performed at a pressure of 60 bar to 80 bar.

15. The method of claim 1, wherein the zeolite has a stability of at least 99% at a temperature of at least 180° C.

16. The method of claim 1, wherein the beta zeolite has a Si/Al$_2$ ratio of 120 or less and/or the beta zeolite has a Si/Al$_2$ ratio of 15 or more.

17. The method of claim 1, wherein the first olefin(s) and/or the second olefin(s) are non-aromatic.

18. The method of claim 1, wherein the method further comprises producing converting the second olefin(s) to produce an article selected from the group consisting of alcohols, aldehydes, plasticizers, mercaptans, adhesives, and surfactants.

19. A method of converting first olefin(s) to second olefin(s), the method comprising: contacting the first olefin(s) with a beta zeolite under oligomerization conditions to convert the first olefin(s) to the second olefin(s),
wherein the first olefin(s) comprises at least one member selected from the group consisting of propylene, butylene, pentene, and mixtures thereof, the second olefin(s) comprises at least two more carbon atoms than the first olefin(s), the beta zeolite has a ratio of external surface area to total surface area of at least 0.65, and the beta zeolite has a stability of at least 99.5% at a temperature of at least 180° C.

20. The method of claim 19, wherein the method is performed at a temperature of at most 300° C.

21. A method of converting first olefin(s) to second olefin(s), the method comprising:
contacting the first olefin(s) with a beta zeolite under oligomerization conditions to convert the first olefin(s) to the second olefin(s),
wherein the method is performed at a temperature of 150° C., the first olefin(s) comprises at least one member selected from the group consisting of propylene, butylene, pentene, and mixtures thereof, the second olefin(s) comprises at least two more carbon atoms than the first olefin(s), the beta zeolite has a ratio of external surface area to total surface area of at least 0.65, and the beta zeolite has a stability of at least 92%.

22. A method of converting first olefin(s) to second olefin(s), the method comprising:
contacting the first olefin(s) with a beta zeolite under oligomerization conditions to convert the first olefin(s) to the second olefin(s) at a conversion of at least 85%,
wherein the first olefin(s) comprises at least one member selected from the group consisting of propylene, butylene, pentene, and mixtures thereof, the second olefin(s) comprises at least two more carbon atoms than the first olefin(s) and the beta zeolite has a ratio of external surface area to total surface area of at least 0.65.

23. A method of converting first olefin(s) to second olefin(s), the method comprising:
contacting the first olefin(s) with a zeolite under oligomerization conditions to convert the first olefin(s) to the second olefin(s),
wherein the first olefin(s) comprises at least one member selected from the group consisting of propylene, butylene, pentene, and mixtures thereof, and the second olefin(s) comprises at least two more carbon atoms than the first olefin(s);
wherein the zeolite comprises a first beta zeolite having a ratio of external surface area to total surface area of at least 0.65; and
wherein, at a temperature, the first beta zeolite has a stability that is greater than a stability a second beta zeolite having a ratio of external surface area to total surface area of less than 0.65 when the second beta zeolite is contacted with the first olefins under the same conditions as the oligomerization conditions.

24. The method of claim 23, wherein, at the temperature, the stability of the first beta zeolite is at least 5% greater than the stability of the second beta zeolite.

* * * * *